(12) United States Patent
Birkholz et al.

(10) Patent No.: US 7,744,997 B2
(45) Date of Patent: Jun. 29, 2010

(54) WATER CONTACT INDICATOR

(75) Inventors: Russell D. Birkholz, Maplewood, MN (US); Paul R. LaBrosse, Forest Lake, MN (US); James S. Mrozinski, Oakdale, MN (US); Ramon T. Ignacio, Somerville, NJ (US)

(73) Assignee: 3M Innovative Properties Company, St. Paul, MN (US)

( * ) Notice: Subject to any disclaimer, the term of this patent is extended or adjusted under 35 U.S.C. 154(b) by 780 days.

(21) Appl. No.: 11/460,407

(22) Filed: Jul. 27, 2006

(65) Prior Publication Data

US 2006/0263597 A1 Nov. 23, 2006

Related U.S. Application Data

(62) Division of application No. 09/972,124, filed on Oct. 5, 2001, now Pat. No. 7,105,225.

(51) Int. Cl.
*B32B 7/12* (2006.01)
*G01D 21/00* (2006.01)

(52) U.S. Cl. .............. 428/354; 428/189; 428/343; 428/351; 428/913; 73/73; 116/206

(58) Field of Classification Search ............. 428/343; 436/2, 164; 422/58, 61; 600/367
See application file for complete search history.

(56) References Cited

U.S. PATENT DOCUMENTS

| | | | |
|---|---|---|---|
| RE24,906 E | 12/1960 | Ulrich | |
| 3,844,718 A | 10/1974 | Cohen | |
| 4,577,205 A | 3/1986 | Shibata et al. | |
| 4,743,238 A | 5/1988 | Colon et al. | |
| 4,935,288 A | 6/1990 | Honaker et al. | |
| 5,238,623 A | 8/1993 | Mrozinski | |
| 5,389,426 A | 2/1995 | Arens et al. | |
| 5,518,763 A | 5/1996 | Patnode et al. | |
| 5,660,925 A | 8/1997 | Cooley et al. | |
| 5,747,146 A | 5/1998 | Kashiwazaki et al. | |
| 5,948,546 A * | 9/1999 | Bafford et al. | 428/500 |
| 6,117,530 A | 9/2000 | Jonza et al. | |
| 6,461,422 B1 | 10/2002 | Yang et al. | |
| 7,105,225 B2 * | 9/2006 | Birkholz et al. | 428/354 |

(Continued)

FOREIGN PATENT DOCUMENTS

EP 1 001 264 A1 5/2000

(Continued)

OTHER PUBLICATIONS

Advantec Laboratory Filter Paper Data Sheet.*

*Primary Examiner*—Jennifer McNeil
*Assistant Examiner*—Adam C Krupicka
(74) *Attorney, Agent, or Firm*—Bradford B. Wright (57) ABSTRACT

The present invention discloses an adhesive article. The adhesive article comprises a first layer comprising a transparent film, the first layer having a first major surface and a second major surface. Additionally, the adhesive article comprises a second layer comprising a fluid transport substrate, the second layer having a first major surface and a second major surface, the first major surface of the second layer being in contact with the second major surface of the first layer and a third layer comprising a fluid transportable ink, the third layer being associated with the second major surface of the second layer. The adhesive article then comprises an adhesive layer.

8 Claims, 2 Drawing Sheets

U.S. PATENT DOCUMENTS

| | | |
|---|---|---|
| 2002/0061391 A1 | 5/2002 | Hayashi et al. |
| 2003/0096107 A1 | 5/2003 | Birkholz et al. |
| 2005/0118415 A1 | 6/2005 | LaBrosse et al. |

FOREIGN PATENT DOCUMENTS

| | | |
|---|---|---|
| EP | 1 043 377 A2 | 10/2000 |
| JP | 61-250535 | 11/1986 |
| JP | 06-202560 | 7/1994 |
| JP | 07-098279 | 4/1995 |
| JP | 07-098309 | 4/1995 |
| JP | 08-254953 | 10/1996 |
| JP | 09-325698 | 12/1997 |
| JP | 10-090244 | 4/1998 |
| JP | 10-254360 | 9/1998 |
| JP | 2000-106596 | 4/2000 |
| JP | 2000-122546 | 4/2000 |
| JP | 2000-151776 | 5/2000 |
| JP | 2001-007907 | 1/2001 |
| JP | 2001-051600 | 2/2001 |
| JP | 2002-311837 | 10/2002 |
| WO | WO 98/23920 | 6/1998 |
| WO | WO 02/43965 A2 | 6/2002 |
| WO | WO 03/031531 A1 | 4/2003 |

* cited by examiner

EXAMPLE 3

0 HOURS

288 HOURS

WATER CONTACT

*Fig. 4*

WATER CONTACT INDICATOR

CROSS REFERENCE TO RELATED APPLICATIONS

This application is a divisional of U.S. Ser. No. 09/972,124, filed Oct. 5, 2001, now U.S. Pat. No. 7,105,225, the disclosure of which is herein incorporated by reference.

FIELD OF THE INVENTION

The present invention relates to adhesive articles having the capability to detect fluid, especially water, exposure.

BACKGROUND OF THE INVENTION

An adhesive article, for example a tape or a label that indicates fluid exposure is desirable for many uses. For example, such an adhesive article may help detect minor leaks in water tight pipes. Additionally, these adhesive articles may be useful for detecting water exposure of electronics, especially hand-held electronics. For example, an adhesive article that indicates water exposure would be useful for manufacturers of electronic devices, for example cellular phones, personal digital assistants, hand held computers, battery chargers, or small electric appliances, to help determine functional failure. The adhesive article may be placed on the electronic device, either within the electronic portion of the device or on an external casing. If the device had been immersed or a sensitive component contacted with a fluid, such as water, the warranty could be voided or the cause of failure determined.

Some adhesive articles used for fluid indication describe a layer of ink on a substrate. The ink is displayed in a pattern that is altered upon exposure to water. For example, the ink may be in stripes or dots, which blur upon exposure to water. Some additional adhesive articles have a transparent cover film to prevent smudging of the ink prior to water exposure. Other adhesive articles utilize an ink that changes color upon the exposure to water.

SUMMARY OF THE INVENTION

Some commercially available adhesive articles indicate too easily under high humidity conditions. Some additional commercially available adhesive articles may not indicate water contact at all after exposure to high humidity conditions. What is desired is a water indicating adhesive article that will indicate upon sustained water exposure, but does not indicate in a high humidity environment.

The present invention discloses an adhesive article. The adhesive article comprises a first layer comprising a transparent film, the first layer having a first major surface and a second major surface. Additionally, the adhesive article comprises a second layer comprising a fluid transport substrate, the second layer having a first major surface and a second major surface, the first major surface of the second layer being in contact with the second major surface of the first layer and a third layer comprising a fluid transportable ink, the third layer being associated with the second major surface of the second layer. The adhesive article then comprises an adhesive layer.

DETAILED DESCRIPTION OF THE INVENTION

Figure 1:
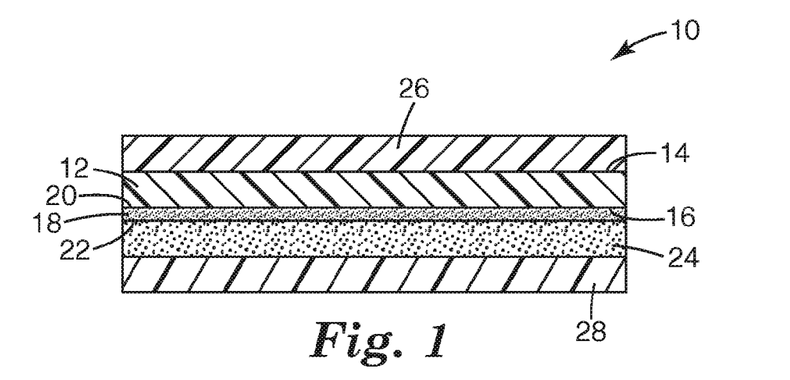
FIG. 1 is a cross-sectional view of a first embodiment of the invention.

An embodiment of the fluid indicating adhesive article is illustrated in FIG. 1. The adhesive article 10 comprises a fluid transport substrate 12 having a first major surface 14 and a second major surface 16. A fluid transportable ink layer 18 is coated onto the second major surface 16 of the substrate 12. The ink layer has a first major surface 20 and a second major surface 22. The first major surface 20 of the ink layer 18 is in contact with the second major surface 16 of the substrate 12. The adhesive article 10 additionally comprises an adhesive layer 24 applied onto the second major surface 22 of the ink layer 18.

The adhesive article 10 additionally comprises a transparent layer 26 laminated onto the first major surface 14 of the substrate 12. The adhesive article 10 also comprises a release liner 28 set on the adhesive layer 24 opposite the second major surface 22 of the ink layer 18.

Figure 2:
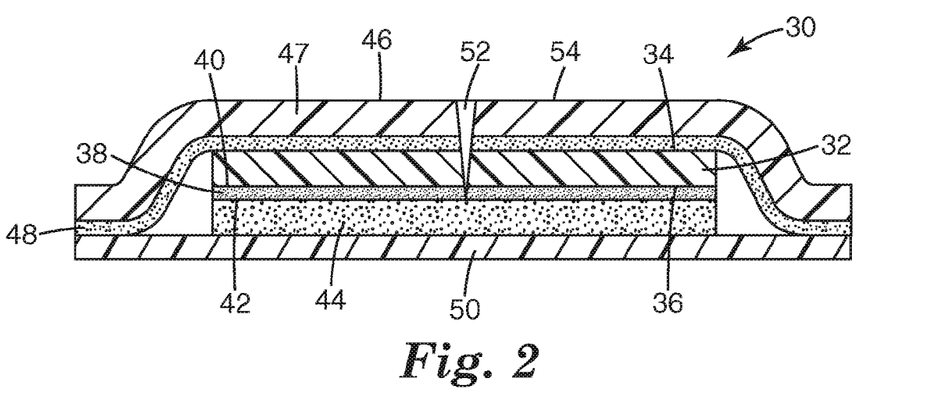
FIG. 2 is a cross-sectional view of a second embodiment of the invention.

Another embodiment of the invention is illustrated in FIG. 2. The adhesive article 30 comprises a substrate 32 having a first major surface 34 and a second major surface 36. An ink layer 38 is coated onto the second major surface 36 of the substrate 32. The ink layer has a first major surface 40 and a second major surface 42. The first major surface 40 of the ink layer 38 is in contact with the second major surface 36 of the substrate 32. The adhesive article 30 additionally comprises an adhesive layer 44 applied onto the second major surface 42 of the ink layer 38.

The adhesive article 30 additionally comprises a transparent layer 46. The transparent layer 46 as illustrated in FIG. 2 comprises a transparent film 47 and a transparent layer adhesive layer 48. The transparent layer adhesive layer 48 is in contact with the first major surface 34 of the substrate 32. The adhesive article 30 also comprises a release liner 50 set on the adhesive layer 44 opposite the second major surface 42 of the ink layer 38. The transparent layer adhesive layer 48 extends past the substrate 32 and is in contact with the release liner 50.

The transparent layer 46, the substrate 32, and the ink layer 38 define a hole 52. The hole 52 exposes the ink layer 38 to an outer surface 54 of the adhesive article 30.

Details of the components of the adhesive article of the present invention are further described below.

Substrate

The fluid indicating adhesive article of the present invention includes a substrate capable of fluid transport ("fluid transport substrate".) A fluid transport substrate will transport fluid through the substrate. For example, the substrate may comprise a microporous film as described in U.S. Pat. No. 5,238,623 to Mrozinski, which is incorporated by reference. In many embodiments, the fluid transport substrate is a fibrous substrate. The fibrous substrate is generally capable of absorbing a fluid. However, the fibrous substrate generally will not saturate in a high humidity environment. In certain embodiments, the substrate is a water absorbent substrate. The water absorbent substrate is generally made of a material that maintains a cohesive form when wet. Suitable substrates include paper, such as cellulose based paper, for example paper towels and copy grade paper.

Additionally, woven and nonwoven fabrics and polyolefins may be suitable substrates. Polyolefins may be treated to enhance fluid absorbance, for example by treating with a hydrophilic coating or blending the polyolefin with a hydrophilic fiber. However, any coating used to make the polyolefin hydrophilic should be chosen so it will not interfere with, or react negatively to the adhesive chosen. Melt-blown or spunbond techniques can be employed to make such nonwoven webs. Nonwoven webs can also be prepared, for example, on a RANDO WEBBER (Rando Corporation, Macedon, N.Y.) air-laying machine or on a carding machine.

Representative examples polyolefins include, for example, polypropylene, polyethylene, high density polyethylene, low density polyethylene, linear low density polyethylene, and linear ultra low density polyethylene, and polybutylenes. Additional materials that may be useful for the substrate of the present invention include nylon, polyester (e.g., polyethylene terephthalate), vinyl copolymers, such as polyvinyl chlorides, both plasticized and unplasticized, and polyvinyl acetates; olefinic copolymers, such as ethylene/methacrylate copolymers, ethylene/vinyl acetate copolymers, acrylonitrile-butadiene-styrene copolymers, and ethylene/propylene copolymers; acrylic polymers and copolymers; polycaprolactones; and combinations of the foregoing. Mixtures or blends of any plastic or plastic and elastomeric materials such as polypropylene/polyethylene, polyurethane/polyolefin, polyurethane/polycarbonate, polyurethane/polyester, can also be used.

Specific examples of suitable substrates include a cellulose paper, such as Westvaco Ultrasorb FP "matte", absorbent cellulose paper commercially available from Westvaco Corp. of Wickliffe, Ky. The substrate may also be a standard weight copy paper, such as paper sold under the tradename COPY-PLUS Standard White, available from International Paper, Memphis, Tenn.

In many embodiments, the water absorbent substrate is flat. The substrate may be clear, white, or any color. Generally, the substrate is opaque when dry, so the layers under the substrate are not visible. In many embodiments, the substrate is permanently opaque, even when wet.

Fluid Transportable Ink

Fluid transportable ink is coated onto one surface of the substrate to form an ink layer. Ink is defined as a dispersion of a pigment or a dye solution produced as a fluid, paste or a powder. Upon exposure to a fluid, the fluid transportable ink is mobilized and flows with the fluid through the substrate. In some embodiments, a hole in the substrate exposes the ink and assists in the displacement of the ink in the event of fluid exposure.

For example, a water soluble ink is suitable for the present invention. In specific embodiments, the ink may be HP Ink Jet cartridge 51649a printed blue ink, commercially available from Hewlett Packard Co., Boise, Id. Other examples include blue dye powder sold under the tradename HIDACID AZURE Blue dustless 20DA2228 commercially available from B.F. Goodrich, Cincinnati, Ohio and red dye sold under the tradename FASTUSOL Red 43LN commercially available from BASF Corp. of Mount Olive, N.J.

The ink may be dispersed on the substrate. In other embodiments, the ink is dispersed on the adhesive layer, which is then brought into contact with the substrate. The ink may be dispersed using various coating and printing techniques chosen to be suitable for a particular ink. For example, the ink may be dispersed using an ink jet printer, gravure printing, flexographic printing, letter press printing or powder coating techniques. The ink may be dispersed on the substrate in a variety of coverage, for example a predetermined pattern, a random pattern, or complete coverage.

Adhesive

An adhesive layer is applied, for example coated or laminated, onto the surface of the ink layer. The adhesive may be any adhesive, for example a thermally bondable (hot-melt) adhesive or an ultra-violet activated adhesive. Generally, the adhesive layer is a pressure sensitive adhesive. Pressure sensitive adhesives are generally characterized by their properties. Pressure sensitive adhesives are well known to one of ordinary skill in the art to possess properties including the following: (1) aggressive and permanent tack, (2) adherence to a substrate with no more than finger pressure, (3) sufficient ability to hold onto an adherend, and (4) sufficient cohesive strength to be removed cleanly from the adherend. Many pressure sensitive adhesives must satisfy these properties under an array of different stress rate conditions. Additives may be included in the pressure sensitive adhesive to optimize the characteristics of the pressure sensitive adhesive.

Any suitable pressure sensitive adhesive composition can be used for this invention. Generally, the pressure sensitive adhesive should not interfere with the ability of the ink to transport with a fluid, for example by reacting with a treatment on the substrate. The pressure sensitive adhesive component can be any material that has pressure sensitive adhesive properties. Furthermore, the pressure sensitive adhesive component can be a single pressure sensitive adhesive or the pressure sensitive adhesive can be a combination of two or more pressure sensitive adhesives.

Pressure sensitive adhesives useful in the present invention include, for example, those based on natural rubbers, synthetic rubbers, styrene block copolymers, polyvinyl ethers, poly (meth)acrylates (including both acrylates and methacrylates), polyolefins, and silicones.

The pressure sensitive adhesive may be inherently tacky. If desired, tackifiers may be added to a base material to form the pressure sensitive adhesive. Useful tackifiers include, for example, rosin ester resins, aromatic hydrocarbon resins, aliphatic hydrocarbon resins, and terpene resins. Other materials can be added for special purposes, including, for example, oils, plasticizers, antioxidants, ultraviolet ("UV") stabilizers, hydrogenated butyl rubber, pigments, and curing agents.

In one embodiment, the pressure sensitive adhesive is based on at least one poly(meth)acrylate (e.g. is a (meth) acrylic pressure sensitive adhesive). Poly(meth)acrylic pressure sensitive adhesives are derived from, for example, at least one alkyl (meth)acrylate ester monomer such as, for example, isooctyl acrylate, isononyl acrylate, 2-methyl-butyl acrylate, 2-ethyl-hexyl acrylate and n-butyl acrylate; and at least one optional co-monomer component such as, for example, (meth)acrylic acid, vinyl acetate, N-vinyl pyrrolidone, (meth)acrylamide, a vinyl ester, a fumarate, a styrene macromer, or combinations thereof. Generally, the poly (meth)acrylic pressure sensitive adhesive is derived from between about 0 and about 20 weight percent of acrylic acid and between about 100 and about 80 weight percent of at least one of isooctyl acrylate, 2-ethyl-hexyl acrylate or n-butyl acrylate composition, preferably isooctyl acrylate. A suitable embodiment for the present invention is derived from between about 2 and about 10 weight percent acrylic acid and between about 90 and about 98 weight percent of at least one of isooctyl acrylate, 2-ethyl-hexyl acrylate or n-butyl acrylate composition.

The adhesive layer is applied onto the ink layer using any suitable coating or laminating technique. For example, the adhesive layer may be formed by continuous forming methods, including hot melt coating, drawing or extruding, the adhesive composition from the elongating shear force device (e.g. a draw die, a film die, or a rotary rod die) and subsequently contacting the drawn adhesive composition to a moving web (e.g. plastic) or other suitable substrate. A related continuous forming method involves extruding the adhesive composition and a co-extruded backing material from a film die and cooling the layered product to form an adhesive tape. Other continuous forming methods involve directly contacting the adhesive composition to a rapidly moving web or other suitable preformed substrate. Using this method, the adhesive composition is applied to the moving preformed web using a die having flexible die lips, such as a rotary rod die. The adhesive layer may additionally be formed by any non-continuous coating method.

Alternatively, the adhesive may be prepared by dissolving the components of the adhesive composition in a solvent such as toluene and casting over the substrate.

Transparent Layer

The water indicating adhesive article of the present invention additionally has a transparent layer comprising a transparent film on the fluid transporting substrate. The transparent layer is on the substrate surface opposite the ink layer. The transparent layer may extend beyond the edge of the substrate, or may be the same size as the substrate. Generally such a layer may be waterproof. Such a layer protects the water indicating adhesive article from moisture during human handling and from dew/condensation. Additionally, the additional layer may protect the water indicating adhesive article during prolonged submersion and may extend the life of certain water indicating tapes during humidity aging conditions. In certain embodiments, the transparent layer is printable using a variety of printing techniques, including ink-jet printing, thermal transfer printing and flexographic printing. In addition, the transparent layer may be a multi-layer decorative film such as, for example, those disclosed in U.S. Pat. No. 6,117,530 to Jonza et al.

The transparent layer may have an adhesive layer, as detailed in FIG. 2, to adhere the transparent layer to the substrate. Alternatively, the transparent layer may be adhered to the substrate by high temperature lamination, thus eliminating the need for an adhesive layer between the substrate and the transparent layer. The transparent layer serves to protect the adhesive article surface from dirt, debris, and handling contaminants as well as holding the color within the paper when the indicator is immersed in water for long periods. When an adhesive article without a protective film is immersed for long periods of time, one potential problem is that it will bleed out or wash out and start to turn back to the original, non-indicating color (white); thus giving a false reading that it was not exposed to water. Also, depending upon the material of the substrate, an adhesive article without a protective film may begin to disintegrate if immersed for long periods of time. However, an adhesive article with a protective cover film will hold the color change in the paper and will not bleed out or disintegrate after long periods of time immersed. Specific examples of transparent layers suitable for the present invention include UPVC backed tapes, such as those sold under the tradename Scotch Premium Transparent Film Tape 600; polypropylene tapes such as those sold under the tradename Scotch Box Sealing Tape 375 and polyester backed tapes such as those sold under the tradename Scotch Box Sealing Tape 355, or 3M™ Thermal Transfer Imprintable Film Tape 7861; all commercially available from 3M Company of St. Paul, Minn.

Additional Layers

The water indicating tape of the present invention may comprise additional layers. For example, some embodiments comprise an additional fluid transport substrate layer between the adhesive layer and the ink layer. The water indicating tape may also comprise a release liner, such as silicone coated paper or film, adhered to the adhesive until the tape is ready to be adhered to a surface.

If the tape is sold in a roll, it may be beneficial to add a release material (e.g., low adhesion backsize) to the side of the tape opposite the adhesive.

Method of Manufacture

The water indicating adhesive article of the present invention is manufactured generally by coating a substrate as described with a fluid transportable ink. The substrate may be in the form of a sheet, or may be a long strip suitable for rolling the final product into a roll of tape. The ink may be coated to completely cover the substrate, or may be coated in segments or a design. The ink must be coated so that the ink does not bleed through the substrate. For example, the ink may be coated onto a release liner, and then transferred to the substrate.

Adhesive is then applied to the ink as described above. The substrate and the ink may then be completely coated with the adhesive, or may be coated with segments of adhesive. Such a segmented adhesive may be desirable in embodiments where the substrate may have a coating that may be affected by the adhesive. The adhesive is then covered with a release liner if desired.

In other embodiments, the adhesive can be made into a transfer tape by coating the adhesive composition, either completely or in segments, on a liner, or between two liners, coated with a release coating. If the transfer tape is made by coating between two liners, one of the liners of the transfer tape can be removed to expose the adhesive surface. The adhesive surface may then be applied to the ink layer, or the adhesive surface may be coated with the fluid transportable ink and then laminated to the substrate. The remaining release liner aids in transferring the adhesive to the substrate.

Individual labels may be created by converting the sheets into individual labels, for example by die cutting the sheet. The sheet may be die cut into any size or shape, such as circles or squares. For example, the sheet may be die cut into a circle with a diameter greater than 5 millimeters for ease of handling. Specific examples include rectangles used for an informative label, or small circles placed inside an electronic device.

Figure 3:
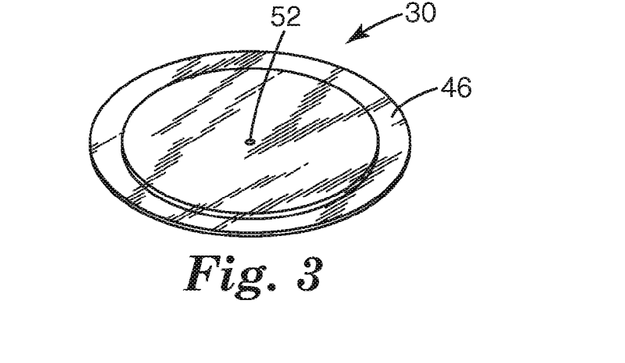
FIG. 3 is a perspective view of the embodiment shown in FIG. 2.

The transparent layer may be laminated or adhered to the substrate prior to converting the substrate into an individual label. In separate embodiments, the transparent layer is added to the adhesive article after conversion, for example in embodiments as depicted in FIG. 2 wherein the transparent layer extends beyond the edge of the substrate. The embodiment illustrated in FIGS. 2 and 3 may be manufactured by cutting a label, for example by die cutting, around the existing adhesive article, creating an overlap of the transparent film as seen in FIGS. 2 and 3.

Use of the Adhesive Article

The adhesive article of the present invention may be a roll of tape. The adhesive article may also be an individual label. In these embodiments, the adhesive article is placed on a device, such as a portable electronic device. In some embodiments, the adhesive article is printed, for example the adhesive article could include warranty information in addition to acting as an indicator for fluid exposure.

Upon exposure to a fluid, the adhesive article of the present invention exposes to indicate the fluid contact. Depending on the ink and the substrate used in the adhesive article, the fluid could include polar solvents such as alcohol, non-polar solvents, bodily fluids and water. Generally, the adhesive article can indicate exposure to a fluid if the ink is soluble in the fluid and the fluid transports through the substrate. Specifically, the invention is beneficial to indicate the exposure to fluids containing water, such as consumable alcoholic drinks.

Objects and advantages of this invention are further illustrated by the following examples. The particular materials and amounts thereof, as well as other conditions and details, recited in these examples should not be used to unduly limit this invention.

EXAMPLES

Materials:

| Item | Description | Supplier |
| --- | --- | --- |
| Substrate B | Westvaco Ultrasorb FP "matte," absorbent, cellulose paper | Westvaco Corporation of Wickliffe, Kentucky |
| Substrate C | Hammermill CopyPlus Copy Paper, 8 ½" × 11", 84 Brightness | International Paper of Memphis, Tennessee |
| Ink-Blue | Inkjet "Blue" from HP Inkjet cartridge 51649a | Hewlett Packard Co., of Boise, Idaho |
| Ink-Red | FASTUSOL Red 43LN | BASF Corp of Mount Olive, New Jersey |
| Laminating Adhesive | 3M ™ 467MP Roll Laminating Adhesive | 3M Company of St. Paul, Minnesota |
| Transparent Protective Film | Scotch ® Premium Transparent Film Tape 600 | 3M Company of St. Paul, Minnesota |
| Transparent Protective Film | 3M ™ Thermal Transfer Imprintable Film Label Material 7861, 2.0 mil Gloss Clear Polyester Thermal Transfer, 0.8 mil 300 high strength acrylic adhesive, 3.2 mil 55# densified Kraft liner | 3M Company of St. Paul, Minnesota |
| Transparent Protective Film | 3M ™ Thermal Transfer Imprintable Film Label Material 7876, 2.0 mil Gloss Clear Polyester Thermal Transfer, 1.8 mil 350 high strength acrylic adhesive, 3.2 mil 55# densified Kraft liner | 3M Company of St. Paul, Minnesota |

The following examples describe the making and testing of a water contact indicator. It is understood that in all the examples, the order of the process may be altered to achieve the same final construction of the various embodiments of the present invention.

First Embodiment of the Invention

Examples of the First Embodiment

Example 1 was prepared by taking a sheet of Ultrasorb FP "matte", absorbent, cellulose paper, referred to here as Substrate B, and cutting it into a separate master sheet to fit into an Inkjet printer, model Hewlett Packard DeskJet 692C. Substrate B has a caliper thickness of approximately 5.8 mil (0.147 mm), a Sheffield porosity value of approximately 25 seconds and opacity of approximately 92%. The paper substrate was then solid printed over the entire surface of one side with a water-soluble blue colored ink, HP Inkjet "Blue" using a model 692C Hewlett Packard DeskJet. The printed side of the paper was laminated to a laminating adhesive using 3M™ 467MP Roll Laminating Adhesive, 2.0 mil (50 microns) #200MP "Hi-Performance" Acrylic Adhesive with a 4.0 mil (100 microns) release liner of 58# Tan Polycoated Kraft Paper. Scotch® Premium Transparent Film Tape 600, was applied to the non-printed side of the paper.

Individual water contact indicators were then created from the master sheet by die cutting the sheet into 13-mm diameter circles, although any size and shape indicator could be prepared, by standard converting steps.

Example 2 was prepared in the same manner as example 1, with the exception that an 8½×11 inch (21.6 cm×27.9 cm) piece of Hammermill CopyPlus Copy Paper, was used instead of the Ultrasorb FP "matte", absorbent, cellulose paper.

Example 3 was prepared in the same fashion as example 1, except that the paper substrate was gravure printed with FASTUSOL Red 43LN red ink prior to the application of the laminating adhesive.

Example 4 was prepared exactly as example 1, however instead of the Scotch® Premium Transparent Film Tape 600, the transparent cover sheet used was 3M™ Thermal Transfer Imprintable Film Label Material 7876, 2.0 mil Gloss Clear Polyester Thermal Transfer, 1.8 mil 350 high strength acrylic adhesive.

Example 5 was prepared exactly as example 1, however instead of the Scotch® Premium Transparent Film Tape 600, the transparent cover sheet used was 3M™ Thermal Transfer Imprintable Film Label Material 7861, 2.0 mil Gloss Clear Polyester Thermal Transfer, 0.8 mil 300 high strength acrylic adhesive.

Several replicates of each of the above examples were generated for testing and evaluation purposes. The examples were tested for their indicating functionality under conditions of high humidity and total water contact. To test for sensitivity to a high humidity environment, a number of replicates of each example were stored hanging vertically in a controlled temperature/humidity chamber at 158° F. (70° C.)/90% relative humidity. At periodic intervals, individual replicates of the various examples were removed from the temperature/humidity chamber and evaluated for their change in color using a HUNTERLAB Labscan 600 Spectrocolorimeter, available from Hunter Associates Laboratory, Inc., of Reston, Va. Data was obtained by following test method Tappi T 524 om-94, measuring the change in the darkness of a color in terms of an L value where the L scale is defined as 100 being white and 0 being black.

EXAMPLES

| Example | Description |
| --- | --- |
| 1 | Paper "B", ink jet printed blue, #600 cover film |
| 2 | Copy paper, ink jet printed blue, #600 cover film |
| 3 | Paper "B", gravure printed red ink, #600 cover film |
| 4 | Paper "B", ink jet printed blue, #7876 cover film |
| 5 | Paper "B", ink jet printed blue, #7861 cover film |

TABLE 1

HUMIDITY EXPOSURE vs. WATER CONTACT
Humidity Conditions: 70° C./90% Relative Humidity Data:

| Example | 0 hrs | 5 hrs | 24 hrs | 48 hrs | 144 hrs | 288 hrs | Water Contact* Value (1 min) |
|---|---|---|---|---|---|---|---|
| 1 | 89.58 | 89.09 | 86.16 | 81.87 | 77.5 | — | 57.90 |
| 2 | 86.81 | 83.74 | 76.34 | 71.54 | — | — | 62.51 |
| 3 | 88.90 | 89.85 | 89.32 | 89.34 | — | 88.35 | 49.24 |

"L" Scale Data: "L" scale denotes color shade change from white = 100 to black = 0
*Contact of samples for 1 minute in water.
"—" Not measured at these time points.

TABLE 2

RELATIVE CHANGE IN SAMPLE DARKNESS FROM ORIGINAL
AFTER EXPOSURE TO HUMIDITY AND IMMERSION

| Example | % Change Humidity | % Change Water Contact | Water Contact vs. Humidity color change factor |
|---|---|---|---|
| 1 | 13.5% | 35.4% | 2.6 |
| 2 | 17.6% | 28.0% | 1.6 |
| 3 | 0.6% | 44.6% | 74.3 |

Figure 4:
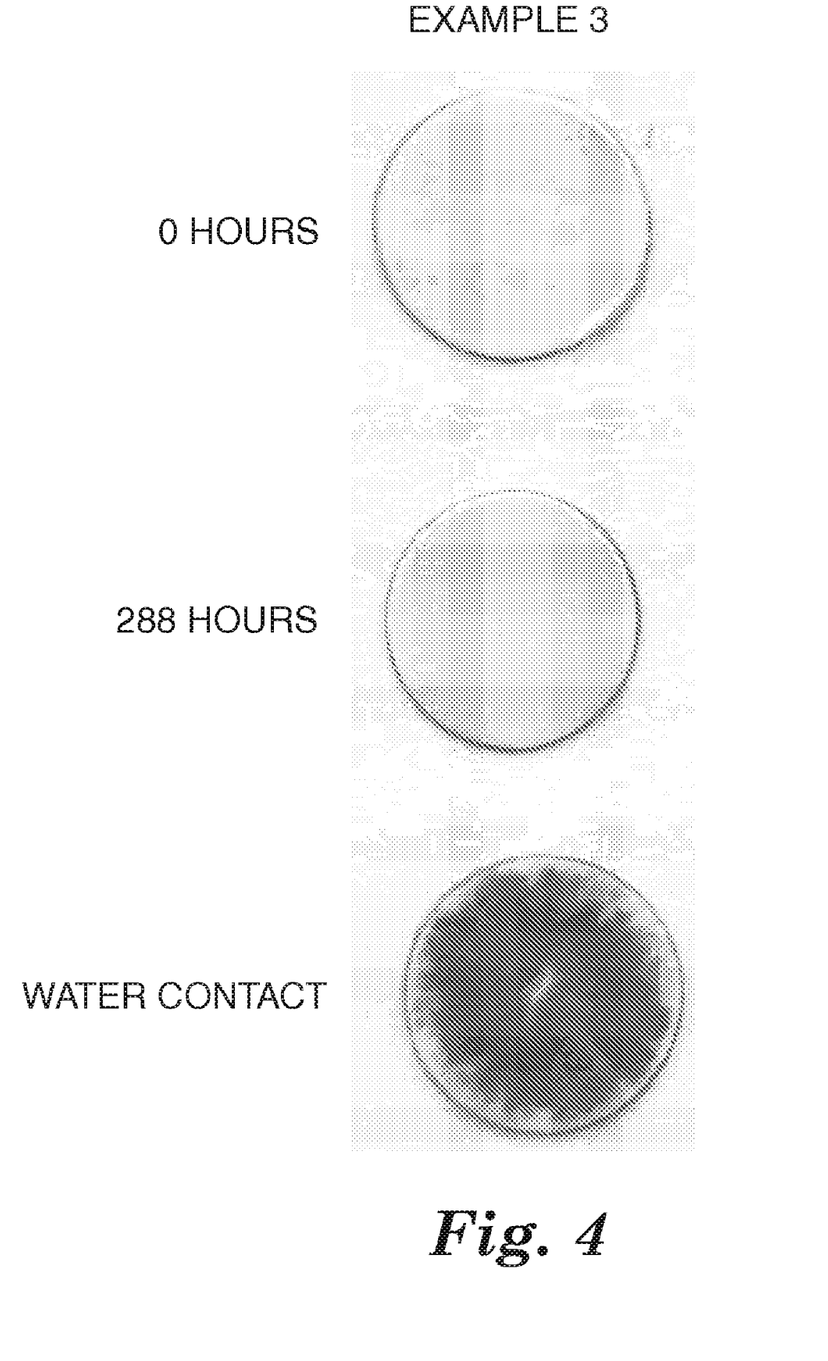
FIG. 4 is a digitally recorded micrograph showing example 3 during high humidity exposure as detailed below.

The data in Table 1 shows that most examples exhibit a slight color change with prolonged exposure to high humidity. Table 2 shows the relative change in indicator darkness in L values from the 0-time point to the time of longest humidity exposure for all samples and relative to water contact for 1 minute. Table 2 indicates that all samples remain in a generally non-indicating condition after exposure to high humidity. However, the L value for examples after water contact is much lower, indicating much darker, than the L value for examples exposed to high humidity. This is also clearly illustrated by FIG. 4, where example 3, after 288 hours of exposure to high humidity, is essentially unchanged, but after just 1 minute of water contact, there is a dramatic change in the darkness of the color of example 3.

Table 3 demonstrates the potential problem with "washout." Comparative Example A was made as described for Example 3, without a transparent layer. After total immersion in water for 48 hours, Comparative Example A, which has no protective film has reached an indication plateau, even slightly less indication from 24 hours to 48 hours. The indicating ink has begun to "washout." Whereas, example 3, which has a protective cover film, holds the color change and continues to strongly indicate immersion even after extended exposure.

TABLE 3

EXTENDED TOTAL IMMERSION EXPOSURE

| Example | 0 hrs | 4 hrs | 24 hrs | 48 hrs |
|---|---|---|---|---|
| Comp. Ex. A | 91.34 | 73.69 | 69.12 | 70.57 |
| 6 | 89.14 | 77.04 | 65.5 | 55.41 |

| Example | Description |
|---|---|
| Comp. Ex. A | Paper "B", gravure printed red ink, No protective film |
| 6 | Paper "B", gravure printed red ink, #600 cover film |

TABLE 4

HUMIDITY EXPOSURE OF SAMPLES WITH
VARIOUS PROTECTIVE FILMS
Humidity Conditions: 70° C./90% Relative Humidity

| Example | 0 hrs | 24 hrs | 72 hrs | 168 hrs | Water Contact* Value (1 min) |
|---|---|---|---|---|---|
| 4 | 88.59 | 85.94 | 83.41 | 79.62 | 51.76 |
| 5 | 89.35 | 86.95 | 80.96 | 76.24 | 51.76 |

"L" Scale Data: "L" scale denotes color shade change from white = 100 to black = 0
*Water Contact of samples for 1 minute in water.

| Example | Description |
|---|---|
| 4 | Paper "B", ink jet printed blue, #7876 cover film |
| 5 | Paper "B", ink jet printed blue, #7861 cover film |

Second Embodiment of the Invention

Another embodiment of the water contact indicator of the present invention includes the following modification to the general embodiment described in examples 1-5. The ink is applied to the substrate sheet in a pattern such as parallel stripes or lines that are about 0.25 inch wide each, rather than a solid printed pattern over the entire surface of one side. The striped printed side of the substrate is then laminated to a laminating adhesive, as in examples 1-8. The sheet is then cut or slit into strips, each wider than the width of the printed stripe. Thus, leaving a non-printed area on each side of the stripe. A transparent protective film is then applied to the non-printed side in a manner such that the transparent protective film covers and is wider than the width of the strip of substrate. This strip construction of water contact indicator can then be cut at any length for application. Indication will happen at the newly cut strip ends where the paper edge is not covered by the transparent protective film and so may be exposed to water.

Third Embodiment of the Invention

As in examples 1-5 of the first embodiment, ink applied to a substrate surface. Also, the printed side of the substrate is then laminated to a laminating adhesive with a liner. This construction is then die cut in circular shapes and the non-circular shaped matrix paper and adhesive is removed leaving only the die cut printed substrate circles on the liner. A transparent protective film or laminate is then laminated over the die cut parts and exposed liner. Next, another die cut conversion process is performed to leave the printed substrate circle centrally located within this second die cut and having the transparent cover extending equally around the paper. At this point no edge or portion of the printed paper circle is exposed. These die cut parts are then perforated with a die-punched hole in the center of the individual circular water contact indicator. This die-punched hole perforates the protective film layer and the substrate layer, down to the printed ink layer. When this embodiment of the water contact indicator is exposed to water, the hole acts as an access to the indicator where the water is absorbed and indication is observed. The size of the die-punched hole is small enough to minimize "false" contact indications due to high humidity.

Various modifications and alterations that do not depart from the scope and spirit of this invention will become apparent to those skilled in the art. This invention is not to be unduly limited to the illustrative embodiments set forth herein.

What is claimed is:

1. A water contact indicating system comprising
an adhesive article comprising
    a first layer comprising a transparent film and an adhesive, the first layer having a first major surface and a second major surface;
    a second layer comprising a fluid transport substrate, the second layer having a first major surface and a second major surface, the first major surface of the second layer being partially in contact with the second major surface of the first layer and partially exposed; and
    a third layer comprising a fluid transportable ink, the third layer being associated with the second major surface of the second layer; and
    a device in contact with the third layer,
wherein the first layer extends beyond the second and third layers so that the adhesive is in contact with the device; and wherein there is a hole through the first layer exposing the second layer.

2. The article of claim 1 wherein the device is a personal electronic device.

3. The adhesive article of claim 1 wherein the substrate is water absorbent.

4. The adhesive article of claim 1 wherein the substrate is porous.

5. The adhesive article of claim 1 wherein the substrate is a cellulose-based paper.

6. The adhesive article of claim 1 wherein the fluid transportable ink comprises a water soluble ink.

7. The adhesive article of claim 1 wherein the fluid transportable ink comprises a dye.

8. The adhesive article of claim 1 wherein the first layer further comprises indicia printed on the first major surface.

* * * * *

UNITED STATES PATENT AND TRADEMARK OFFICE
CERTIFICATE OF CORRECTION

PATENT NO. : 7,744,997 B2  Page 1 of 1
APPLICATION NO. : 11/460407
DATED : June 29, 2010
INVENTOR(S) : Russell D Birkholz

It is certified that error appears in the above-identified patent and that said Letters Patent is hereby corrected as shown below:

<u>Column 8</u>
Line 47, delete "600" and insert -- 6000 --, therefor.

<u>Column 10</u>
Line 17 (approx.), delete "51.76" and insert -- 49.17 --, therefor.

Signed and Sealed this

Sixteenth Day of November, 2010

David J. Kappos
*Director of the United States Patent and Trademark Office*